(12) United States Patent
Robin et al.

(10) Patent No.: US 6,849,194 B2
(45) Date of Patent: Feb. 1, 2005

(54) METHODS FOR PREPARING ETHERS, ETHER COMPOSITIONS, FLUOROETHER FIRE EXTINGUISHING SYSTEMS, MIXTURES AND METHODS

(75) Inventors: Mark Robin, West Lafayette, IN (US); Thomas F. Rowland, El Dorado, AR (US); John Chien, West Lafayette, IN (US); Janet Boggs, Brownsburg, IN (US); Mitchel Cohn, West Lafayette, IN (US); Vicki Hedrick, Brookston, IN (US); Stephan Brandstadter, Indianapolis, IN (US)

(73) Assignee: PCBU Services, Inc., Wilmington, DE (US)

( * ) Notice: Subject to any disclaimer, the term of this patent is extended or adjusted under 35 U.S.C. 154(b) by 0 days.

(21) Appl. No.: 10/435,455

(22) Filed: May 12, 2003

(65) Prior Publication Data

US 2003/0209685 A1 Nov. 13, 2003

Related U.S. Application Data

(63) Continuation-in-part of application No. PCT/US01/44256, filed on Nov. 14, 2001, application No. 10/435,455.
(60) Provisional application No. 60/249,684, filed on Nov. 17, 2000, and provisional application No. 60/390,202, filed on Jun. 20, 2002.

(51) Int. Cl.[7] .......................... A62D 1/08; C09K 5/00; A62C 2/00; A62C 3/00; C07C 43/12
(52) U.S. Cl. .............................. 252/8; 252/2; 252/364; 252/77; 169/45; 169/46; 169/47; 568/681; 568/683; 568/684; 568/685; 510/411; 510/412
(58) Field of Search ................................ 252/2, 8, 364, 252/77; 169/45, 46, 47; 510/411, 412; 568/681, 683, 684, 685

(56) References Cited

U.S. PATENT DOCUMENTS

| | | |
|---|---|---|
| 2,671,799 A | 3/1954 | Miller |
| 2,730,543 A | 1/1956 | Rendall et al. |
| 2,795,601 A | 6/1957 | Rendall et al. |
| 2,856,435 A | 10/1958 | Lo |
| 2,862,024 A | 11/1958 | Rendall et al. |
| 2,975,163 A | 3/1961 | Lo |
| 3,291,844 A | 12/1966 | Watson |
| 3,362,180 A | 1/1968 | Eiseman |
| 3,476,860 A | 11/1969 | Croix et al. |
| 3,527,814 A | 9/1970 | Croix et al. |

(List continued on next page.)

FOREIGN PATENT DOCUMENTS

| | | |
|---|---|---|
| DE | 25 24 956 A1 | 6/1975 |
| DE | 25 24 956 | 12/1976 |
| DE | 0 005 810 A1 | 5/1979 |

(List continued on next page.)

OTHER PUBLICATIONS

D.B. Bivens and B.H. Minor *Fluoroethers and Other Next-Generation Fluids*, Ashrae/nist Refrigerants Conference, Refrigerants for the 21st Century, Oct. 6 and 7, 1997, pp. 122–134.

(List continued on next page.)

*Primary Examiner*—Joseph D. Anthony
(74) *Attorney, Agent, or Firm*—Wells St. John P.S.

(57) ABSTRACT

Highly fluorinated, saturated, and unsaturated fluoroethers are efficient, economical, non-ozone-depleting fire extinguishing agents used alone or in blends with other fire extinguishing agents in total flooding and portable systems. Methods for producing ethers, halogenated ether intermediates, and fluoroethers are disclosed. Novel fluoroether compositions are disclosed. Fluoroether extinguishing mixtures, methods, and systems are disclosed.

23 Claims, 1 Drawing Sheet

U.S. PATENT DOCUMENTS

| | | | |
|---|---|---|---|
| 3,557,294 A | | 1/1971 | Dear et al. |
| 3,897,502 A | * | 7/1975 | Russell et al. ............... 568/683 |
| 3,943,256 A | * | 3/1976 | Regan ......................... 514/722 |
| 3,976,788 A | * | 8/1976 | Regan ......................... 514/722 |
| 4,014,799 A | | 3/1977 | Owens |
| 4,126,631 A | | 11/1978 | Krespan et al. |
| 4,273,728 A | | 6/1981 | Krespan |
| 4,273,729 A | | 6/1981 | Krespan |
| 4,292,449 A | | 9/1981 | Krespan |
| 4,295,225 A | | 10/1981 | Pan |
| 4,349,650 A | | 9/1982 | Krespan |
| 4,357,282 A | | 11/1982 | Anderson et al. |
| 4,874,901 A | | 10/1989 | Halpern et al. |
| 5,023,009 A | | 6/1991 | Merchant |
| 5,026,498 A | | 6/1991 | Merchant |
| 5,137,932 A | | 8/1992 | Behme et al. |
| 5,169,873 A | | 12/1992 | Behme et al. |
| 5,182,342 A | | 1/1993 | Feiring et al. |
| 5,382,704 A | | 1/1995 | Krespan et al. |
| 5,420,368 A | * | 5/1995 | Jackson et al. ............. 570/142 |
| 5,449,837 A | | 9/1995 | Krespan et al. |
| 5,466,879 A | | 11/1995 | Cheburkoval |
| 5,474,657 A | * | 12/1995 | Hansen ........................ 205/430 |
| 5,484,546 A | | 1/1996 | Minor et al. |
| 5,516,946 A | | 5/1996 | Jackson et al. |
| 5,552,074 A | | 9/1996 | Patron et al. |
| 5,573,654 A | | 11/1996 | Cheburkov et al. |
| 5,594,159 A | | 1/1997 | Jackson et al. |
| 5,611,210 A | | 3/1997 | Nimitz et al. |
| 5,648,560 A | | 7/1997 | Marraccini et al. |
| 5,718,293 A | | 2/1998 | Flynn et al. |
| 5,730,894 A | | 3/1998 | Minor |
| 5,741,950 A | | 4/1998 | Costello |
| 5,750,797 A | | 5/1998 | Vitcak et al. |
| 5,804,162 A | | 9/1998 | Kabalnov et al. |
| 5,919,393 A | * | 7/1999 | Flynn et al. .................... 252/2 |
| 5,977,237 A | | 11/1999 | Shin et al. |
| 5,993,682 A | * | 11/1999 | Tapscott et al. ............... 252/8 |
| 6,001,796 A | | 12/1999 | Pham et al. |
| 6,022,842 A | | 2/2000 | Owens et al. |
| 6,023,002 A | * | 2/2000 | Behr et al. ................... 568/685 |
| 6,028,066 A | | 2/2000 | Unger |
| 6,043,201 A | | 3/2000 | Milbrath et al. |
| 6,090,800 A | | 7/2000 | Unger et al. |
| 6,120,751 A | | 9/2000 | Unger |
| 6,143,276 A | | 11/2000 | Unger |
| 6,149,980 A | | 11/2000 | Behr et al. |
| 6,191,328 B1 | | 2/2001 | Kitano et al. |
| 6,193,952 B1 | | 2/2001 | Kabalnov et al. |
| 6,214,253 B1 | * | 4/2001 | Moore et al. ................. 252/70 |
| 6,253,577 B1 | | 7/2001 | Arman et al. |
| 6,294,508 B1 | | 9/2001 | Milbrath et al. |
| 6,416,683 B1 | | 7/2002 | Klug et al. |
| 6,495,293 B1 | | 12/2002 | Arai et al. |
| 6,552,090 B1 | * | 4/2003 | Behr et al. .................... 516/25 |
| 2001/0031243 A1 | | 10/2001 | Unger |
| 2001/0031740 A1 | | 10/2001 | Unger et al. |
| 2002/0040975 A1 | | 4/2002 | Goble |

FOREIGN PATENT DOCUMENTS

| | | |
|---|---|---|
| DE | 28 23 969 | 12/1979 |
| EP | 0 556 722 A1 | 2/1993 |
| EP | 0 562 858 A1 | 9/1993 |
| EP | 07025803 | 1/1995 |
| GB | 1250928 | 7/1969 |
| GB | 1 469 423 * | 4/1977 |
| GB | 1571356 A | 7/1980 |
| GB | 2 058 763 A | 4/1981 |
| JP | 56-90026 | 7/1981 |
| JP | 56-138127 | 10/1981 |
| JP | 57-85339 | 5/1982 |
| JP | 58-57340 | 4/1983 |
| JP | 58-126837 | 7/1983 |
| JP | 60-184067 | 9/1985 |
| JP | 61-69745 | 4/1986 |
| JP | 62-96441 | 5/1987 |
| JP | 63-35539 | 2/1988 |
| JP | 63-303950 | 12/1988 |
| JP | 3-744 | 1/1991 |
| JP | 3-81239 | 4/1991 |
| JP | 3-229731 | 10/1991 |
| JP | 3-229735 | 10/1991 |
| JP | 4-202242 | 7/1992 |
| JP | 8-37024 | 2/1996 |
| JP | 8-259995 | 10/1996 |
| JP | 8-291299 | 11/1996 |
| JP | 9-110738 | 4/1997 |
| JP | 10-130184 | 5/1998 |
| JP | 10-152573 | 6/1998 |
| JP | 10-223614 | 8/1998 |
| JP | 11-35626 | 2/1999 |
| JP | 11-116524 | 4/1999 |
| JP | 11-124352 | 5/1999 |
| JP | 11-219944 | 8/1999 |
| JP | 99-276949 | 9/1999 |
| JP | 2000-191578 | 7/2000 |
| WO | WO 93/24586 | 12/1993 |
| WO | WO93-24586 | 12/1993 |
| WO | WO94/09083 | 4/1994 |
| WO | WO94/17153 | 8/1994 |
| WO | WO 96/40834 | 12/1996 |
| WO | WO 97/05211 | 2/1997 |
| WO | WO97/33016 | 9/1997 |
| WO | WO97/39081 | 10/1997 |
| WO | WO98/12286 | 3/1998 |
| WO | WO98-33479 | 8/1998 |
| WO | WO98/36449 | 8/1998 |
| WO | WO99/06616 | 2/1999 |
| WO | WO 99/14175 | 3/1999 |
| WO | WO00/66575 A3 | 11/2000 |
| WO | WO 01/05468 A2 | 1/2001 |
| WO | WO 01/27235 A1 | 4/2001 |
| WO | WO02/03958 A1 | 1/2002 |

OTHER PUBLICATIONS

J. Adcock, et al. *Fluorinated Ethers, A New Family of Halons?*, Proceedings of the Halon Alternatives Technical Working Conference, Albuquerque, NM, Apr. 30—May 1, 1991, pp. 83–97.

J. Amer. Chem. Soc., 70, vol. LXX, (1948), pp. 1297, 1550–1552.

J. Amer. Chem. Soc., vol. 73(1951), pp. 507, 861–862.

J. Amer. Chem. Soc., vol. 73(1951), pp. 507, 711–712.

J. Amer. Chem. Soc., vol. 78(1956), pp. 1521, 1685–1686.

A. Sekiya, et al., *The potential of hydrofluoroethers to replace CFCs, HCFCs and PFCs*, J. Fluorine Chem., 101, 215–221 (2000).

Knunyants, I.L., et al., Izvestiya Akademii Nauk SSSR, Seriya Khimicheskaya (1953), 282–9 (Chemical Abstracts 48:32423); Bargamova, et al., Knunyants, I.L., Inst. Elem. –Organ. Soedin., Moscow, USSR. Izvestiy Akademii Nauk SSSR, Seriya Khimicheskaya (1967), (3), 611–14.

(Chemical Abstracts 67:108109); and Shanghai Institute of Organic Chemistry, Shanghai, Peop. Rep. China. Huaxue Xuebao (1976), 34(1), 53–8. Chemical Abstracts 86:170817.

Fukaya, et al., *Fire extinguishing ability of perfluoroalkylamines and perfluoroethers evaluated by a small cup burner method*; Journal of Fluorine Chemistry 106 (2000) 143–146.

R.C. Terrell et al.: "General Anesthetics. I Halogenated methyl ethyl ethers as anesthetic agents". J Medicinal Chem, vol. 14, No. 6, 1971, pp. 517–519.

J.D. Park et al.: 'Directed chlorination of fluorinated aliphatic ethers' J of American Chem Soc., vol. 74, 1952, pp. 2292–2294.

R.C. Terrell et al.: "General Anesthetics 3. Fluorinated methyl ethyl ethers as anesthetic agents". J Medicinal Chem, vol. 15, No. 6, 1972, pp. 604–606.

K. K. Johri et al.: 'Comparison of the reactivity of CF3OX (X=Cl, F) with some simple alkenes' J. Org. Chem. vol. 48, 1983, pp. 242–250.

V.A. Petrov: 'New synthesis of hydrofluoroethers.' J. Fluorine Chem, vol. 112, 2001, pp. 117–121.

B.B. Randolph et al.: 'Synthesis of functionalized polyfluoroaklyl hypochlorites and fluoroxy compounds and their reactions with some fluoroalkens.' J. Fluorine Chem, vol. 64, 1993, pp. 129–149.

Database Beilstein, Beilstein Institute for Organic Chemistry, Frankfurt–Main, DE; XP002287175 Database Accession No. 8203460 abstract.

Database Beilstein, Beilstein Institute for Organic Chemistry, Frankfurt–Main, DE; XP002287176 Database Accession No. 2642703 abstract.

Database Beilstein Institute for Organic Chemistry, Frankfurt–Main, DE; XP002287177 Database Accession No. 4744596 abstract (Update Date Oct. 20, 1993).

Database Beilstein, Beilstein Institute for Organic Chemistry, Frankfurt–Main, DE; XP002287178 Database Accession No. 5429529 abstract (Update Date Feb. 18, 1994).

Database Beilstein, Beilstein Institute for Organic Chemistry, Frankfurt–Main, DE; XP002287179 Database Accession No. 2454312 abstract (Update Date Jan. 21, 1994).

Database Beilstein, Beilstein Institute for Organic Chemistry, Frankfurt–Main, DE; XP002287180 Database Accession No. 1856325 abstract (Update Date Apr. 28, 1997).

International Search Report for PCT/US 03/19693 (2004).

A. L. Henne et al. "Fluorinated ethers" J.AM.CHEM SOC., vol. 72, 1972, pp. 4378–4380.

V.A. Gubanov et al.: "Reaction of hexafluoropropene with (perfluorooalkyl) methanols" J.GEN.CHEM., vol. 35, 1965, pp. 399–400.

Database Crossfire Beilstein Beilstein Institut Zur Forderung der Chemischen Wissenschaften. Database assession no. 5257400 abstract.

V.A. Petrov et al.: J. Fluorine Chem., vol. 95, No. 1, 1999, pp. 5–14.

Partial International Search Results for PCT/US03/19693.

N. Taniguchi, et al. 'Atmospheric Chemistry of $C_2F_5C(O)CF(CF_3)_2$: Photolysis and Reaction with Cl Atoms, OH Radicals, and Ozone' J Phys Chem. A 2003, 107, 2674–2679.

\* cited by examiner

METHODS FOR PREPARING ETHERS, ETHER COMPOSITIONS, FLUOROETHER FIRE EXTINGUISHING SYSTEMS, MIXTURES AND METHODS

RELATED PATENT DATA

This patent is a continuation-in-part of international application PCT/US01/44256, filed Nov. 14, 2001, entitled "Fire Extinguishing Methods Utilizing Hydrofluoroethers," which claims priority to U.S. provisional patent application No. 60/249,684, filed Nov. 17, 2000, having the same title; this patent also claims priority to U.S. provisional patent application No. 60/390,202, filed Jun. 20, 2002, entitled "Ethers and Materials and Methods for Producing and Using the Same."

TECHNICAL FIELD

The present invention is directed to novel ether compounds and in particular aspects halogenated ether compounds and in other embodiments fluorinated ether compounds. Other aspects of the present invention are also directed to the production of these ether compounds and their uses.

Certain aspects of the present invention are directed to hydrofluoroether fire extinguishing agents and methods for extinguishing fires using the hydrofluoroethers. Aspects of the present invention are directed to fire extinguishing agents and methods using saturated or unsaturated, fluorinated $C_4$ and/or $C_5$ hydrofluoroethers, and blends of one or more of the hydrofluoroethers with one or more other fire extinguishing agents.

BACKGROUND OF THE INVENTION

The use of certain bromine, chlorine, and iodine containing halogenated chemical agents for the extinguishment of fires is common. These agents are in general thought to be effective due to their interference with the normal chain reactions responsible for flame propagation. The most widely accepted mechanism for flame suppression is the radical trap mechanism proposed by Fryburg in Review of Literature Pertinent to Fire Extinguishing Agents and to Basic Mechanisms Involved in Their Action, NACA-TN 2102 (1950). The finding that the effectiveness of the halogens are on a molar basis in the order Cl<Br<I supports the radical trap mechanism, as reported by Malcom I Vaporizing Fire Extinguishing Agents, Report 117, Dept. of Army Engineering Research and Development Laboratories, Fort Bevoir, Va., 1950 (Project-8-76-04-003). It is thus generally accepted that compounds containing the halogens Cl, Br and I act by interfering with free radical or ionic species in the flame and that the effectiveness of these halogens is in the order I>Br>Cl. In addition, it is generally thought that to be effective as a fire extinguishing agent, a compound must contain Cl, Br or I.

The use of iodine-containing compounds as fire extinguishing agents has been avoided primarily due to the expense of their manufacture or due to toxicity considerations. Until very recently, the three fire extinguishing agents presently in common use were all bromine-containing compounds; Halon 1301 ($CF_3Br$), Halon 1211 ($CF_2BrCl$) and Halon 2402 ($BrCF_2CF_2Br$). The effectiveness of these three volatile bromine-containing compounds in extinguishing fires has been described in U.S. Pat. No. 4,014,799 to Owens. Certain chlorine containing compounds are also known to be effective extinguishing agents, for example Halon 251 ($CF_3CF_2Cl$) as described by Larsen in U.S. Pat. No. 3,844,354.

Although the above-named bromine or chlorine-containing Halons are effective fire fighting agents, those agents containing bromine or chlorine are asserted by some to be capable of the destruction of the earth's protective ozone layer. Also, because the agents contain no hydrogen atoms which would permit their destruction in the troposphere, the agents may also contribute to the greenhouse warming effect.

More recently, hydrofluorocarbons have been proposed for fire suppression, for example in U.S. Pat. No. 5,124,053. However, a disadvantage of these compounds is their relatively high global warming potential.

Recently, ethers, particularly fluoroethers, have been identified as compounds that may be useful as halon replacements. Typically, these compounds are synthesized with all of the necessary fluorine content in place.

It is therefore an object of this invention to provide a method for extinguishing fires that extinguishes fires as rapidly and effectively as the techniques employing Halon agents while avoiding the above-named drawbacks.

It is a further object of this invention to provide an agent for the use in a method of the character described that is efficient, economical to manufacture, and environmentally safe with regard to ozone depletion and greenhouse warming effects.

It is a still further object of this invention to provide blends of the new agents and other fire extinguishing agents that are effective and environmentally safe.

SUMMARY OF THE INVENTION

One embodiment of the present invention provides processes for producing ethers from olefins and alcohols. In one aspect, the present invention provides processes for producing ethers from olefins and methanol. In a particular aspect, the present invention provides a continuous process of producing ethers by combining olefins and alcohols in the presence of an aqueous solution containing a base.

Another aspect of the present invention provides processes for the production of halogenated ether intermediates useful in the production of fluoroethers. In one aspect, the halogenated ether intermediate can be produced by combining the ether with a halogenating agent in the presence of ultraviolet (uv) radiation.

In a further aspect of the present invention, halogenated ether intermediates can be converted to fluoroethers. In one aspect, $CF_3CHFCF_2OCCl_3$ can be fluorinated in the presence of gaseous HF and a catalyst to produce $CF_3CHFCF_2OCF_3$. In one aspect, $CF_3CHFCF_2OCHF_2$ can be produced by reacting $CF_3CHFCF_2OCHCl_2$ with HF in the presence of a catalyst.

In another aspect, the halogenated ether intermediate can be fluorinated in the presence of liquid hydrogen fluoride (HF) to obtain the fluoroether intermediate which can subsequently be fluorinated to form a fluoroether. In an exemplary aspect, $CF_3CHFCF_2OCCl_3$ can be fluorinated in the presence of liquid HF to form $CF_3CHFCF_2OCCl_2F$ which can subsequently be fluorinated in the presence of gaseous HF to form $CF_3CHFCF_2OCF_3$.

The hydrofluoroethers of this invention may be produced via numerous routes. For example, $CF_3CHFCF_2OCF_2H$ may be prepared via a three step process comprising:
i. reaction of methanol with commercially available hexafluoropropene ($CF_3CF{=}CF_2$) in the presence of base to produce $CF_3CHFCF_2OCH_3$;

ii. chlorination of $CF_3CHFCF_2OCH_3$ with $Cl_2$ to produce $CF_3CHFCF_2OCHCl_2$; and iii. fluorination of $CF_3CHFCF_2OCHCl_2$ with HF to produce the final product $CF_3CHFCF_2OCF_2H$.

By further reacting with a strong base like sodium or potassium hydroxide the corresponding unsaturated $C_4$ or $C_5$ hydrofluoroethers may be prepared.

In still another embodiment of the present invention, ethers of the present invention are used as extinguishants (including streaming and total flooding agents), solvents, refrigerants, blowing agents, etchants, anesthetics, and propellants. Novel compositions of matter such as $CF_3CHFCF_2OCF_3$ are also provided.

The foregoing and other objects, advantages and features of the present invention may be achieved by employing saturated or unsaturated, higher fluorinated hydrofluoroethers and blends thereof with other agents as fire extinguishants for use in fire extinguishing methods and apparatus. More particularly, the method of this invention involves introducing to a fire a saturated or unsaturated, fluorinated $C_4$ or $C_5$ hydrofluoroether in a fire extinguishing concentration and maintaining such concentration until the fire is extinguished. Specific saturated, fluorinated $C_4$ or $C_5$ hydrofluoroethers of this invention include: $CF_3CHFCF_2OCH_3$, $CF_3CHFCF_2OCH_2F$, $CF_3CHFCF_2OCF_2H$, $CF_3CHFCF_2OCF_3$, $(CF_3)_2CHCF_2OCH_3$, $(CF_3)_2CHCF_2OCH_2F$, $(CF_3)_2CHCF_2OCHF_2$, and $(CF_3)_2CHCF_2OCF_3$.

Specific unsaturated, fluorinated $C_4$ or $C_5$ hydrofluoroethers of the present invention include: $CF_3CF=CFOCH_3$, $CF_3CF=CFOCH_2F$, $CF_3CF=CFOCHF_2$, $CF_3CF=CFOCF_3$, $CF_2=CFCF_2OCH_3$, $CF_2=CFCF_2OCH_2F$, $CF_2=CFCF_2OCF_2H$, $CF_2=CFCF_2OCF_3$, $(CF_3)_2C=CFOCH_3$, $(CF_3)_2C=CFOCH_2F$, $(CF_3)_2C=CFOCF_2H$, $(CF_3)_2C=CFOCF_3$, $CF_2=C(CF_3)CF_2OCH_3$, $CF_2=C(CF_3)CF_2OCH_2F$, $CF_2=C(CF_3)CF_2OCF_2H$, and $CF_2=C(CF_3)CF_2OCF_3$.

These hydrofluoroethers may be used alone, in admixture with each other or as blends with other fire extinguishing agents. Generally, the agents of this invention are employed at concentrations lying in the range from about 3 to about 15%, preferably from about 5 to about 10% in air, on a v/v basis. The agents of this invention are suitable for use in both total flooding and portable fire suppression applications. Suitable extinguishing agents ("blends") for admixture with the hydrofluoroethers include $CF_3CHFCF_3$, $CF_3CF_2CF_2H$, $CF_3CH_2CF_3$, $CF_3CF_2H$, and $CF_3H$.

The above and other embodiments, aspects, alternatives, and advantages of the present invention will become more apparent from the following detailed description of the present invention taken in conjunction with the drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

According to an embodiment of the present invention fluoroethers are produced and utilized to extinguish combustion. For purposes of this disclosure the term fluoroethers includes all compounds having an ether group and a fluorine atom. Examples of these compounds include, but are not limited to perfluoroethers, hydrofluoroethers, fluorohalogenated ethers, and/or hydrofluorohalogenated ethers. Exemplary aspects of the present invention are described with reference to FIGS. 1 and 2.

Figure 1:
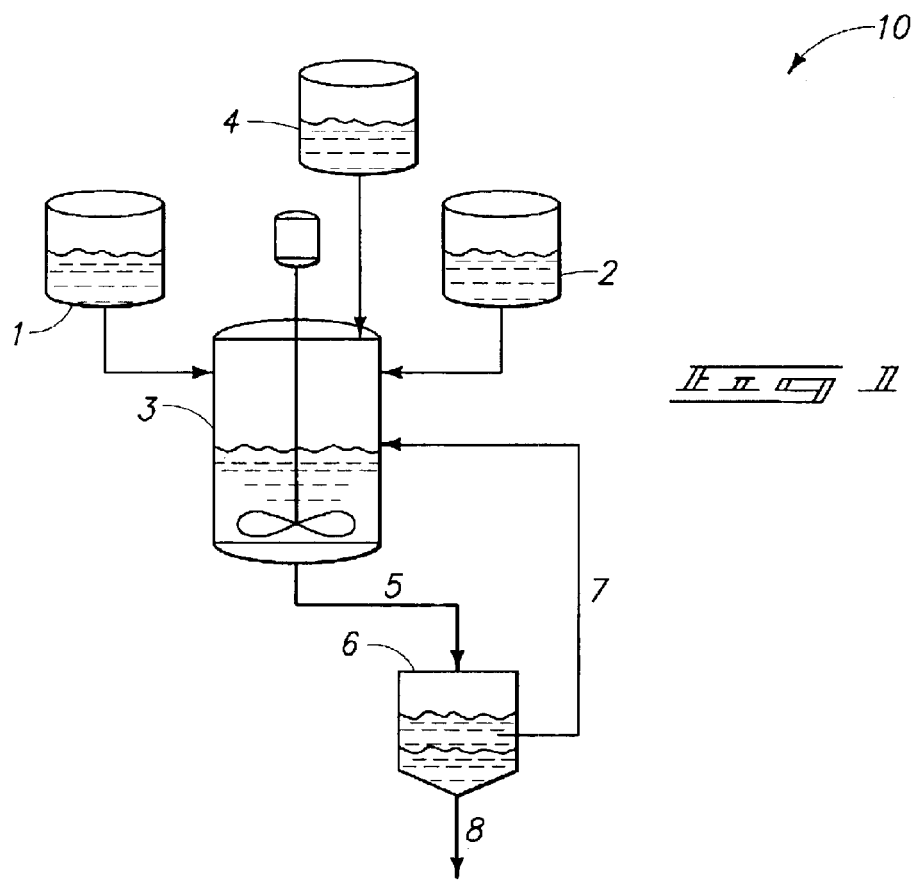
FIG. 1. is a diagram of one embodiment of ether production in accordance with an aspect of the present invention.

Referring now to FIG. 1, a reaction apparatus 10 including a source of olefin 1, a source of alcohol 2, and basic aqueous solution 4 (with the olefin, alcohol, and basic aqueous solution being reagents 7) is shown. The apparatus further includes a reaction vessel 3. In one aspect, olefin 1, alcohol 2, and a basic aqueous solution 4 are combined to form an ether containing reaction product 5. Reagents can be combined in a batch, semi-continuous, or continuous fashion. Reaction product 5 can remain in reaction vessel 3 and/or be transferred to a separation vessel 6, as shown, where a crude ether product 8 is separated from reagents 7. Reagents 7 can then be returned to reaction vessel 3 to react in the presence of additional or remaining basic aqueous solution 4.

Depending on the specific olefins and alcohols selected as starting materials, the ether containing reaction product may be removed from reaction vessel 3 in a number of forms including as a gas or as a top, middle or bottom liquid layer. Likewise, the separation of crude ether 8 from reagents 7 may involve removal of crude ether product 8 as a gas or as a top, middle, or bottom liquid layer and otherwise removal of reagents 7 as a gas or a top, middle, or bottom layer. Consequently, the return of reagents 7 to reaction vessel 3 may take the form of the return of a gas and/or liquid composition.

Olefin 1 can have the general formula $R^1(R^2)C=CXY$. Olefin 1 can generally be referred to as a hydrogenated, halogenated, and/or a perhalogented olefin. $R^1$ can include lone halogens, lone hydrogens, halogenated alkyl groups, hydrogenated alkyl groups or perhalogenated alkyl groups either alone or in combination. For purposes of this disclosure, the halogenated alkyl groups includes all alkyl groups having at least one halogen, regardless of what the remaining elements of the alkyl might be. For example, and by way of example only, halogenated alkyl groups include but are not limited to —CHFCl, —CF$_3$, or —CF$_2$Cl. $R^2$ can include lone halogens, lone hydrogens, halogenated alkyl groups, hydrogenated alkyl groups or perhalogenated alkyl groups either alone or in combination. $R^1$ and $R^2$ can be the same or different groups. In one aspect $R^1$ includes CF$_3$— or F. In one aspect of the present invention, $R^2$ can be H or F. In one combination, $R^1$ can be F and $R^2$ can be F. In another combination, $R^1$ can be F and $R^2$ can be H.

For purposes of this disclosure, X and Y can generally represent hydrogen and/or the halogens I, Br, Cl, and/or F. In one aspect of the present invention, X and Y can be the same element, for example, X can be F and Y can be F. In an exemplary aspect, X and Y can be different elements, for example, X can be F and Y can be H.

According to an aspect of the present invention, olefin 1 includes $CF_3CF=CF_2$ (hexafluoropropene, HFP), $CF_3CH=CF_2$ (pentafluoropropene, PFP), or $CF_2=CF_2$ (tetrafluoroethene, TFE). In certain aspects of the present invention, olefin 1, can comprise, consist, and/or consist essentially of $CF_3CF=CF_2$. In exemplary aspects, olefin 1 can comprise, consist, and/or consist essentially of $CF_2=CF_2$.

Alcohol 2 includes hydrogenated and halogenated alcohols. According to an aspect of the present invention, alcohol 2 can include methanol ($CH_3OH$), ethanol ($CH_3CH_2OH$), and/or isopropanol (($CH_3)_2CHOH$).

Basic aqueous solution 4 can include sufficient base to ensure the formation of an alkoxide upon combination with an alcohol. Bases that can be used to form the alkoxide include those of sodium and potassium such as sodium hydroxide (NaOH) or potassium hydroxide (KOH). In an aspect of the present invention, basic aqueous solution includes KOH.

According to an aspect of the present invention, basic aqueous solution 4 includes an aqueous solution having a KOH concentration of 10–45% (wt./wt.). This KOH solution can be combined with alcohol 2 in reaction vessel 3 to form a first reactant mixture having an alcohol concentration of 50–60% (wt./wt.) and a KOH concentration of 5–20% (wt./wt.). Olefin 1 can then be combined with the first reactant mixture in reaction vessel 3. Reaction vessel 3 can have a temperature from about −10° C. to about 50° C.

According to one aspect, the bottom organic phase containing crude ether 8 can be separated from the top mixture that can include reagents 7. In an exemplary aspect reagents 7 can be returned to reaction vessel 3.

The crude ether 8 of the present invention can generally be referred to as an ether or halogenated ether and have the general formula $R^3CXY$—O—$R^4$. The $R^3$ group can include hydrogenated alkyl groups, halogenated alkyl groups, and/or perhalogenated alkyl groups. For example, and by way of example only, $R^3$ can include $CF_3CHF$—, $CF_3CH_2$—, and/or $CHF_2$—. The $R^4$ group can include hydrogenated alkyl groups, halogenated alkyl groups, and/or perhalogenated alkyl groups. For example, and by way of example only, $R^4$ can include —$CH_3$, —$CH_2CH_3$, and/or —$CH(CH_3)_2$. In an aspect of the present invention, the halogenated ether includes $CF_3CHFCF_2OCH_3$. In another aspect of the present invention, the halogenated ether includes $CF_3CH_2CF_2OCH_3$. In still another aspect of the present invention, the halogenated ether includes $CHF_2CF_2OCH_3$. Non-limiting examples 1–3 demonstrate aspects of ether preparation according to the present invention.

According to another aspect of the present invention a halogenated ether intermediate can be formed by reacting an ether with a halogen in the presence of actinic energy. This reaction can be carried out in a photochemical reactor. The reactor may be configured to provide actinic energy to its content from an internal and/or an external source. For example, and by way of example only, a medium pressure mercury lamp (100 watt, 11.49 watt total radiant energy) can be utilized to provide the necessary radiation from within the reactor. Other configurations may include the use of 90% 3500 angstrom range of photon black light providing 24 watts of total radiant energy. The reactor may be cooled, for example, from a municipal water source.

The halogen can include chlorine ($Cl_2$). Depending on the product desired, halogens such as bromine or iodine may be utilized as well. The reaction can be performed at a temperature from about 10° C. to about 70° C.

In an exemplary aspect, methods include providing a photochemical reactor containing an ether. The ether can have the general formula $R^3CXY$—O—$R^4$, as described above.

The halogenated either intermediate can have the general formula $R^5CXY$—O—$R^6$. The $R^5$ group can include hydrogenated alkyl groups, halogenated alkyl groups, and/or perhalogenated alkyl groups. For example, and by way of example only, $R^5$ can include $CF_3CHF$—, $CF_3CClF$—, $CF_3CH_2$—, $CF_3CHCl$—, $CF_3CCl_2$—, $CHF_2$—, and/or $CClF_2$—. The $R^6$ group can include halogenated alkyl groups or perhalogenated alkyl groups. For example, and by way of example only, $R^6$ can include —$CH_2Cl$, —$CHCl_2$, and/or —$CCl_3$. In an aspect of the present invention, the halogenated ether intermediate can include $CF_3CHFCF_2OCCl_3$. In another aspect of the present invention, the halogenated ether intermediate can include $CF_3CHFCF_2OCHCl_2$. In still another aspect of the present invention, the halogenated ether intermediate can include $CF_3CHFCF_2OCH_2Cl$. In an exemplary aspect, the halogenated ether intermediate can include $CF_3CClFCF_2OCCl_3$.

In certain aspects of the present invention, two halogenated ether intermediates useful in the production of fluoroethers can be produced according to the present invention. In one aspect, the ether $CF_3CHFCF_2OCH_3$ can be chlorinated according to the present invention to produce a mixture of halogenated ether intermediates such as $CF_3CHFCF_2OCHCl_2$ and $CF_3CHFCF_2OCCl_3$. Non-limiting Example 4 demonstrates an aspect of the halogenated ether intermediate production methods according to the present invention.

Another aspect of the present invention provides methods for converting halogenated ether intermediates to useful fluoroethers. Aspects of the present invention provide efficient processes for fluorinating halogenated ethers to produce heretofore unknown compounds.

In an aspect of the present invention, the halogenated ether intermediate can have the general formula $R^5CXY$—O—$R^6$, as described above. In an aspect of the present invention, the halogenated ether intermediate can be selectively fluorinated in the presence of HF and a catalyst to produce a fluoroether.

The catalyst can include a chromium/carbon catalyst that has been pre-fluorinated. The catalyst utilized may take pure or supported forms. Supports include but are not limited to those of activated carbon. The catalysts themselves include but are not limited to such catalysts as those of chromium, nickel, iron, vanadium, manganese, cobalt, and/or zinc. The preparation can occur from about 100° C. to about 300° C. In certain aspects, the temperature of the reaction is about 200° C.

The fluoroether produced can have the general formula $R^7$—O—$R^8$. The $R^7$ group can include hydrogenated alkyl groups, hydrofluorohalogenated alkyl groups, hydrofluorinated alkyl groups, fluorohalogenated alkyl groups, and/or perfluorinated alkyl groups. For example, and by way of example only, $R^7$ can include $CF_3CHFCF_2$—, $CF_3CClFCF_2$—, $CF_3CF_2CF_2$—, $CF_3CH_2CF_2$—, $CF_3CHClCF_2$—, $CF_3CCl_2CF_2$—, $CHF_2CF_2$—, $CF_3CF_2$—, and/or $CClF_2CF_2$—. The $R^8$ group can include hydrofluorohalogenated alkyl groups, hydrofluorinated alkyl groups, fluorohalogenated alkyl groups, and/or perfluorinated alkyl groups. For example, and by way of example only, $R^8$ can include —$CFCl_2$, —$CF_2Cl$, —$CF_3$, —$CHFCl$, —$CF_2H$, and/or $CFH_2$. In an aspect of the present invention, the fluoroether includes the hydrofluoroether $CF_3CHFCF_2OCF_3$. In another aspect of the present invention, the fluoroether includes the hydrofluoroether $CF_3CHFCF_2OCHF_2$. In still another aspect of the present invention, the fluoroether includes the perfluorinated ether $CF_3CF_2CF_2OCF_3$.

According to one aspect of the present invention, an ether can be fluorinated in the presence of liquid hydrogen fluoride (HF). In one aspect, an ether having at least one of the halogens I, Br, or Cl can be fluorinated in the presence of liquid HF to produce a fluoroether. The fluoroether produced according to this aspect of the present invention can be characterized as having at least one more fluorine atom than the ether. For example, and by way of example only, the ether $CF_3CHFCF_2OCCl_3$ can be fluorinated in the presence of liquid HF to produce the fluoroether $CF_3CHFCF_2OCFCl_2$. In one aspect of the present invention, this fluorination can occur from about 40° C. to about 120° C. In one aspect of the present invention, this fluorination can occur at approximately 70° C.

The fluoroether produced according to this aspect of the present invention may be utilized as starting materials for other aspects of the present invention. Accordingly, the ether can be fluorinated at about 70° C. and subsequently fluorinated at about 200° C. The ether may also be fluorinated at about 70° C. and subsequently fluorinated at about 230° C. or 280° C. For example, and by way of example only, the ether $CF_3CHFCF_2OCCl_3$ can be fluorinated in the presence of liquid HF to produce the fluoroether $CF_3CHFCF_2OCFCl_2$, which can be fluorinated in the presence of HF and a catalyst as described above to produce the hydrofluoroether $CF_3CHFCF_2OCF_3$.

An embodiment of the present invention also provides multi-step synthetic processes for the production of fluoroethers. According to one aspect of the present invention, methods are provided for manufacturing fluoroethers that include combining an alcohol with an olefin to produce an ether. Subsequently, reacting the ether with a halogenating agent to produce a halogenated ether intermediate and then fluorinating the halogenated ether intermediate with HF to from a fluoroether. In another aspect, the halogenated ether intermediate can be fluorinated with HF at a first temperature to from a fluoroether intermediate. The fluoroether intermediate can then be fluorinated with HF at a second temperature to form a fluoroether.

An embodiment of the present invention also provides halogenated ether compounds. Generally, these ether compounds have the formula $R^9OR^{10}$. Generally, $R^9$ can be partially or fully halogenated, saturated or unsaturated, organic groups, and $R^{10}$ can be partially or fully halogenated, saturated or unsaturated organic groups. In particular aspects, these halogenated ether compounds include $CF_3CHFCF_2OCF_3$. The structure of $CF_3CHFCF_2OCF_3$ was confirmed by gas chromatography mass spectrometry (GC-MS) and fluorine ($^{19}F$), proton ($^1H$), and carbon ($^{13}C$) nuclear magnetic resonance (NMR). The boiling point of this compound was also determined.

GC-MS (m/e): 69 ($CF_3$), 82 ($CF_3CH$), 101 ($CF_3CHF$), 129 ($CHFCF_2OCF$ or $CHCF_2OCF_2$), 135 ($CF_2OCF_3$), 151 ($CF_3CHFCF_2$), 217 ($CF_3CHFCF_2OCF_2$).

High Resolution MS Theoretical: 235.98837; Found: 235.98726.

NMR: $F^{19}$ (282 MHz, $CFCl_3$): δ −55.4 (t, 3F, J=8.9 Hz), −75.3 (m, 3F), −81.4 (m, 2F), −211.5 (d, t, q, 1F, J=43.64, 10.91 Hz) ppm; $H^1$: (300 MHz, $CDCl_3$): δ 4.86 (d, t, q, 1H, J=43.8, 5.51, 5.98 Hz) ppm; $C^{13}$: (75 MHz, $CDCl_3$): δ 77 (t, J=31.78 Hz), 84.1 (d, t, q, J=204.69, 35.79, 35.79 Hz), 119.2 (q, J=267.68 Hz), 112–125 (m) ppm.

Boiling point: 23–24° C.

Non-limiting Examples 5, 6, 7, and 8 demonstrate preparations according to aspects of the present invention.

The present invention also provides fire extinguishing mixtures which comprise fluoroether extinguishing agents that can extinguish fires through inertion, and/or dilution, as well as, chemical, physical, and/or thermal extinguishment methods. Thermal extinguishment includes "cooling" a combustion. The present invention also provides methods of extinguishing, preventing, and/or suppressing a fire using such fire extinguishing mixtures. The present invention further provides fire extinguishing, preventing, and/or suppressing systems for delivering such fire extinguishing mixtures. Exemplary aspects of the present invention are described with reference to FIG. 2.

Figure 2:
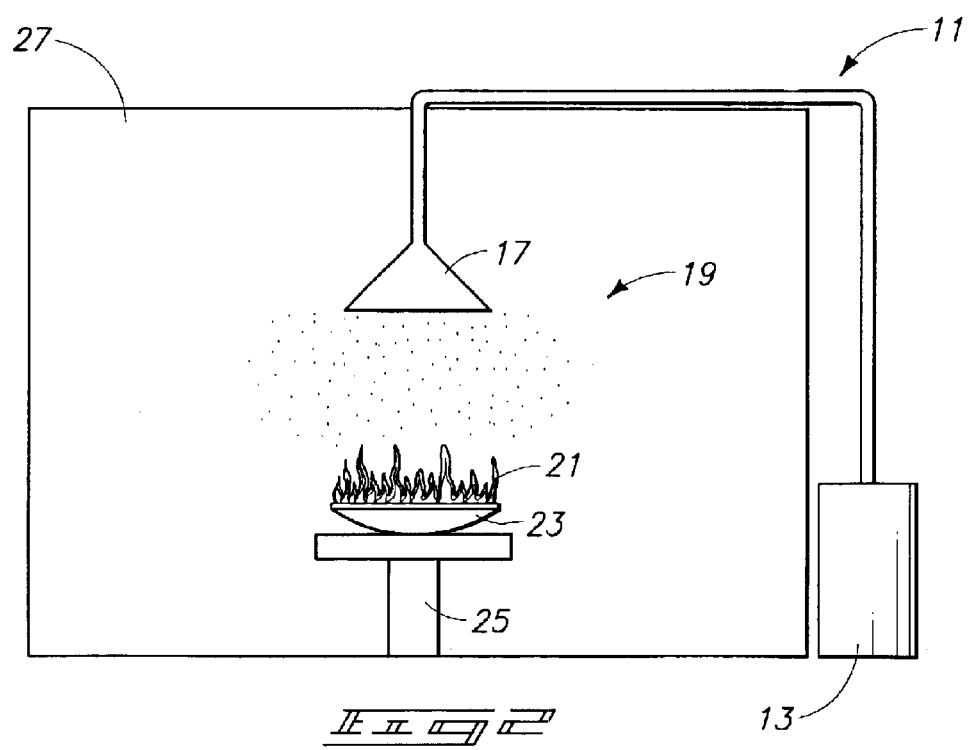
FIG. 2 is an illustration of an application of extinguishing mixtures in accordance with an aspect of the present invention.

Referring to FIG. 2, a space 27 configured with a fire extinguishing system 11 is shown. Fire extinguishing system 11 includes an extinguishing agent storage vessel 13 contiguous with an extinguishing agent dispersing nozzle 17. As depicted, a combustion 21 occurs within a pan 23 on a pedestal 25. An extinguishing mixture 19 exists within space 27 and is applied to combustion 21 to substantially extinguish the flame.

While depicted in two dimensions, space 27, for purposes of this disclosure, should be considered to have a volume determined from its dimensions (e.g., width, height and length). While FIG. 2 illustrates a system configured for extinguishing fires within a space that, as illustrated, appears to be enclosed, the application of the mixtures, systems, and methods of the present invention are not so limited. In some aspects, the present invention may be used to extinguish fires in open spaces, as well as, confined spaces.

All combustion suitable for extinguishment, suppression or prevention using the mixtures of the present invention or utilizing the methods and systems according to the present invention, are at least partially surrounded by a space. The available volume of this space can be filled with the compositions of the present invention to extinguish, suppress, and/or prevent combustion. Typically, the available volume is that volume which can be occupied by a liquid or a gas [i.e. that volume within which fluids (gases and liquids) can exchange]. Solid constructions typically are not part of the available volume.

Furthermore, FIG. 2 illustrates a single extinguishing agent storage vessel 13. It should be understood that extinguishing mixture 19 can be provided to room 27 from multiple extinguishing agent storage vessels 13 and the present invention should not be limited to mixtures, methods, and/or systems that can be provided from a single vessel nor methods or systems that utilize a single vessel. Generally, combustion 21 is extinguished when extinguishing mixture 19 is introduced from vessel 13 through nozzle 17 to space 27. It should also be understood, that while FIG. 2 illustrates a single nozzle 17, multiple nozzles may be utilized, and the present invention should not be limited to mixtures, methods, and/or systems utilizing a single nozzle.

In one aspect of the present invention, extinguishing mixture 19 can comprise, consist essentially of, and/or consist of a fluoroether extinguishing agent. In another aspect, extinguishing mixture 19 can comprise, consist essentially of, and/or consist of a fluoroether extinguishing agent and a suppressing additive and/or other fire extinguishing agents.

The suppressing additive employed can include diluent gases, water, and/or mixtures thereof. Exemplary diluent gases can include nitrogen, argon, helium, carbon dioxide, and/or mixtures thereof. In an exemplary aspect, these gases can deprive fires of necessary ingredients, such as oxygen and/or fuel. In the same or other aspects, these diluent gases resist decomposition when exposed to combustion. In some cases, these gases are referred to as inert gases. An exemplary diluent gas can comprise, consist essentially of, and/or consist of nitrogen.

In accordance with the present invention, the saturated and unsaturated $C_4$ and $C_5$ hydrofluoroethers of the present invention have been found to be effective fire extinguishants at concentrations safe for use.

Specific hydrofluoroethers useful in accordance with this invention are: $CF_3CHFCF_2OCH_3$, $CF_3CHFCF_2OCH_2F$, $CF_3CHFCF_2OCF_2H$, $CF_3CHFCF_2OCF_3$, $(CF_3)_2CHCF_2OCH_3$, $(CF_3)_2CHCF_2OCH_2F$, $(CF_3)_{22}OCHF_2$, $(CF_3)_2CHCF_2OCF_3$, $CF_3CF=CFOCH_3$, $CF_3CF=CFOCH_2F$, $CF_3CF=CFOCHF_2$, $CF_3CF=CFOCF_3$, $CF_2=CFCF_2OCH_3$, $CF_2=CFCF_2OCH_2F$, $CF_2=CFCF_2OCF_2H$, $CF_2=CFCF_2OCF_3$, $(CF_3)_2C=CFOCH_3$, $(CF_3)_2C=CFOCH_2F$, $(CF_3)_2C=CFOCF_2H$, $(CF_3)_2C=CFOCH_3$, $CF_2=C(CF_3)CF_2OCH_3$, $CF_2=C(CF_3)CF_2OCH_2F$, $CF_2=C(CF_3)CF_2OCF_2H$, and $CF_2=C(CF_3)CF_2OCF_3$.

Generally, these ether compounds have the formula $R^9OR^{10}$. Generally, $R^9$ can be partially or fully halogenated, saturated or unsaturated, organic groups, and $R^{10}$ can be partially or fully halogenated, saturated or unsaturated organic groups. More specifically the extinguishing compounds of the present invention can have the general formula $Z^1$—O—$Z^2$. The $Z^1$ group can include $CF_3CHFCF_2$—, $CF_3CF_2CF_2$—, $(CF_3)_2CHCF_2$—, $CHF_2CF_2$—, $CF_2=C(CF_3)$—, $CF_3CF=CF$—, $CF_2=CFCF_2$—, $CF_3CH=CF$—, $CF_3CHBrCF_2$—, $CF_3CFBrCF_2$— or $CF_2BrCF_2$—. The $Z^2$ group can include —$CHF_2$, —$CF_3$, —$CH_2F$, —$CH_2Br$, —$CFBr_2$, —$CHFBr$ or —$CF_2Br$. In particular aspects the extinguishing compound includes $CF_3CHFCF_2OCF_3$ and/or $CF_3CHFCF_2OCHF_2$.

These hydrofluoroethers may be used alone, as admixtures with each other or as blends with other fire extinguishing agents. Generally, when a single hydrofluoroether of this invention is employed, concentrations lying in the range from about 3 to about 15%, preferably from about 5 to about 10% in air, on a v/v basis, are used; when employed as admixtures, concentrations lying in the range from about 3 to about 15%, preferably from about 5 to about 10% in air, on a v/v basis, are used. Where the hydrofluoroethers of this invention are employed in admixture with other fire extinguishing agents ("blends"), the hydrofluoroethers desirably comprise of at least about 10% by weight of the blends, and the overall concentration of the blend lies in the range from about 3 to about 15%, preferably from about 5 to about 10% in air, on a v/v basis. The agents of this invention are suitable for use in both total flooding and portable fire suppression applications. Suitable extinguishing agents for blends with the hydrofluoroethers include $CF_3CHFCF_3$, $CF_3CF_2CF_2H$, $CF_3CH_2CF_3$, $CF_3CHFCF_2H$, $CF_3CF_2H$, and $CF_3H$.

It should be understood that the % (v/v) values set forth in this description and in the claims are based on space volume and refer to the design concentration as adopted and described by the National Fire Protection Association in *NFPA 2001, Standard on Clean Agent Fire Extinguishing,* 2000 edition.

The equation used to calculate the concentrations of extinguishing compounds has likewise been adopted by the National Fire Protection Association and is as follows:

$$W = V/s(C/100-C)$$

Where:

W=weight of extinguishing compound (kg)
V=volume of test space (m$^3$)
s=specific volume of extinguishing compound at test temperature (m$^3$/kg)
C=concentration (% (v/v))

The novel ethers according to the present invention may be used in conjunction with difluoromethane (HFC-32), chlorodifluoromethane (HCFC-22), 2,2-dichloro-1,1,1-trifluoroethane (HCFC-123), 1,2-dichloro-1,1,2-trifluoroethane (HCFC-123a), 2-chloro-1,1,1,2-tetrafluoroethane (HCFC-124), 1-chloro-1,1,2,2-tetrafluoroethane (HCFC-124a), pentafluoroethane (HFC-125), 1,1,2,2-tetrafluoroethane (HFC-134), 1,1,1,2-tetrafluoroethane (HFC-134a), 3,3-dichloro-1,1,1,2,2-pentafluoropropane (HCFC-225ca), 1,3-dichloro-1,1,2,2,3-pentafluoropropane (HCFC-225cb), 2,2-dichloro-1,1,1,3,3-pentafluoropropane (HCFC-225aa), 2,3-dichloro-1,1,1,3,3-pentafluoropropane (HCFC-225da), 1,1,1,2,2,3,3-heptafluoropropane(HFC-227ca), 1,1,1,2,3,3,3-heptafluoropropane (HFC-227ea), 1,1,1,2,3,3-hexafluoropropane (HFC-236ea), 1,1,1,3,3,3-hexafluoropropane (HFC-236fa), 1,1,1,2,2,3-hexafluoropropane (HFC-236cb), 1,1,2,2,3,3-hexafluoropropane (HFC-236ca), 3-chloro-1,1,2,2,3-pentafluoropropane (HCFC-235ca), 3-chloro-1,1,1,2,2-pentafluoropropane (HCFC-235cb), 1-chloro-1,1,2,2,3-pentafluoropropane (HCFC-235cc), 3-chloro-1,1,1,3,3-pentafluoropropane (HCFC-235fa), 1,1,1,3,3-pentafluoropropane (HFC-245fa), 3-chloro-1,1,1,2,2,3-hexafluoropropane (HCFC-226ca), 1-chloro-1,1,2,2,3,3-hexafluoropropane (HCFC-226cb), 2-chloro-1,1,1,3,3,3-hexafluoropropane (HCFC-226da), 3-chloro-1,1,1,2,3,3-hexafluoropropane (HCFC-226ea), 2-chloro-1,1,1,2,3,3-hexafluoropropane (HCFC-226ba), and inert gases such as nitrogen.

The $C_4$ or $C_5$ hydrofluoroethers of this invention may be effectively employed at substantially any minimum concentrations at which fire may be extinguished, the exact minimum level being dependent on the particular combustible material, the particular hydrofluoroether, and the combustion conditions. In general, however, acceptable results are achieved where the hydrofluoroethers or mixtures and blends thereof are employed at a level of at least about 3% (v/v). Where hydrofluoroethers alone are employed, acceptable results are achieved with agent levels of at least about 5% (v/v). Likewise, the maximum amount to be employed will be governed by matters of economics and potential toxicity to living things. About 15% (v/v) provides a convenient maximum concentration for use of hydrofluoroethers and mixtures and blends thereof in occupied areas. Concentrations above 15% (v/v) may be employed in unoccupied areas, with the exact level being determined by the particular combustible material, the hydrofluoroether (or mixture or blend thereof) chosen, and the conditions of combustion. A concentration of the hydrofluoroether agents, mixtures, and blends in accordance with an aspect of this invention lies in the range of about 5 to 10% (v/v).

In particular aspects, an extinguishing mixture comprising, consisting essentially of, and/or consisting of $CF_3CHFCF_2OCF_3$ may be employed. $CF_3CHFCF_2OCF_3$ can be employed at concentrations of about 5% (v/v).

Hydrofluoroethers may be applied using conventional application techniques and methods used for Halons such as Halon 1301 and Halon 1211. Thus, these agents may be used in a total flooding fire extinguishing system in which the agent is introduced to an enclosed region (e.g., a room or other enclosure) surrounding a fire at a concentration sufficient to extinguish the fire. In accordance with the present invention, a total flooding system apparatus, equipment, or even rooms or enclosures may be provided with a source of agent and appropriate piping, valves, and controls so as to automatically and/or manually introduce an appropriate concentration in the event that fire should break out. Thus, as is known to those skilled in the art, the fire extinguishant may be pressurized with nitrogen or other inert gas at up to about 600 psig at ambient conditions.

Alternatively, the hydrofluoroether agents may be applied to a fire through the use of conventional portable fire extinguishing equipment. It is usual to increase the pressure in portable fire extinguishers with nitrogen or other inert gases in order to insure that the agent is completely expelled from the extinguisher. Hydrofluoroether containing systems in accordance with this invention may be conveniently pressurized at any desirable pressure up to about 600 psig at ambient conditions.

The compounds of the present invention are nondestructive agents, and are especially useful where cleanup of other media poses a problem. Some of the applications of the hydrofluoroethers of this invention are the extinguishing of liquid and gaseous fueled fires, the protection of electrical equipment, ordinary combustibles such as wood, paper, and textiles, hazardous solids, and the protection of computer facilities, data processing equipment, and control rooms.

One aspect of the present invention is based on the finding that an effective amount of a composition consisting essentially of the novel ether according to the present invention will prevent and/or extinguish fire based on the combustion of combustible materials, particularly in an enclosed space, without adversely affecting the atmosphere from the standpoint of toxicity to humans, ozone depletion, or "greenhouse effect."

It has been determined that the use of the novel ethers, according to the present invention would comprise a habitable atmosphere, which does not sustain combustion of combustible materials of the non-self-sustaining type. Non-self-sustaining combustible materials include materials which do not contain an oxidizer component capable of supporting combustion.

The novel ethers according to the present invention can also be introduced to a fire for suppression purposes as a liquid or gas or combination of both. This is sometimes referred to as utilizing the composition as a streaming agent. The novel ethers according to the present invention can be introduced to fires in combination with other compounds as blends.

In another aspect, the invention provides a process for preventing and controlling fire in an enclosed air-containing mammalian-habitable compartment which contains combustible materials of the non-self-containing type which comprises (a) introducing the novel ether of the present invention into the air in the enclosed compartment in an amount sufficient to suppress combustion of the combustible materials in the enclosed compartment; and/or (b) introducing oxygen in an amount from zero to the amount required to provide, together with the oxygen present in the air, sufficient total oxygen to sustain mammalian life.

In still another embodiment of the present invention, ethers of the present invention are used either alone or as blends as extinguishants, including streaming and total flooding agents, solvents, refrigerants, blowing or expansion agents, etchants, anesthetics, propellants, and as power cycle working fluids.

The novel ethers of the present invention may be used to produce refrigeration by condensing the ether either alone or as a blend and thereafter evaporating the condensate in the vicinity of a body to be cooled. The novel ether of the present invention may also be used to produce heat by condensing the refrigerant in the vicinity of the body to be heated and thereafter evaporating the refrigerant.

The invention will be further described with reference to the following specific Examples. However, it will be understood that these Examples are illustrative in nature and not restrictive in nature. Where referenced, G.C. area % corresponds to percentage area of peak in comparison to all peaks generated when the respective sample is analyzed by a gas chromatograph equipped with a flame ionization detector and a silica-plot column.

EXAMPLE 1

Ether Preparation

$CF_3CF=CF_2 + CH_3OH \xrightarrow{aq.\ KOH} CF_3CHFCF_2OCH_3$

An aqueous 45% (wt./wt.) KOH solution is added to methanol to produce a mixture containing 60% (wt./wt.) methanol and 18% (wt./wt.) KOH. This mixture is placed in a three-neck glass flask equipped with a dry ice condenser, a dip tube, and a thermometer. HFP is fed through the dip tube into the solution at −3° C. to 0° C. The condenser is kept at −30 to −40° C. in order to condense unreacted HFP back into the reactor. A water bath is used to control the exothermic reaction. When the solution becomes a milky suspension, the mixture is drawn out of the reactor and allowed to phase separate. The bottom organic phase containing crude $CF_3CHFCF_2OCH_3$ is separated out, and the top mixture with additional methanol is fed back to the reactor. Four aliquots of the crude $CF_3CHFCF_2OCH_3$ are collected at time intervals and analyzed by gas chromatography for lights, unreacted olefin, ether, and heavies. The results are shown below in Table 1.

TABLE 1

| | | $CF_3CF=CF_2 + CH_3OH$ Crude Product Col- | aq. KOH | $CF_3CHFCF_2OCH_3$ | |
|---|---|---|---|---|---|
| | | | (G.C. Area %) | | |
| Aliquot | lected (g) | Lights | Olefin $CF_3CF=CF_2$ | $CF_3CHFCF_2OCH_3$ | Heavies |
| A | 22.5 | trace | 4.04 | 89.09 | 6.12 |
| B | 18.5 | 0.46 | 3.49 | 88.72 | 6.73 |
| C | 26.6 | 0.44 | 3.49 | 85.59 | 9.73 |
| D | 97.84 | trace | 5.14 | 87.78 | 6.11 |

Overall Crude Yield 84.9% based on HFP

EXAMPLE 2

Ether Preparation

$CF_3CF=CF_2 + CH_3OH \xrightarrow{aq.\ KOH} CF_3CHFCF_2OCH_3$

Example 2 is performed as Example 1 with the modification that the reaction is performed using an aqueous mixture having 13% (wt./wt.) KOH and 57% (wt./wt.) methanol at 15° C. to 25° C., and two collection aliquots are taken and analyzed by gas chromatography. The gas chromatography results are reported below in Table 2.

TABLE 2

| | aq. KOH | | | | |
|---|---|---|---|---|---|
| $CF_3CF=CF_2 + CH_3OH$ | → | | $CF_3CHFCF_2OCH_3$ | | |

| | Crude Product Collected | G.C. Area % | | | |
|---|---|---|---|---|---|
| Aliquot | (g) | Lights | Olefin $CF_3CF=CF_2$ | $CF_3CHFCF_2OCH_3$ | Heavies |
| A | 77.2 | trace | 0.65 | 94.99 | 3.68 |
| B | 45 | trace | 1.69 | 95.08 | 2.12 |

EXAMPLE 3

Ether Preparation $$CF_2=CF_2 + CH_3OH \xrightarrow{aq.\ KOH} CHF_2CF_2OCH_3$$

Example 3 is performed as example 1 with the modification that the reaction is performed in a 600 cc stainless steel pressure reactor using an aqueous mixture having 10% (wt./wt.) KOH and 50% (wt./wt.) methanol. The reactor is cooled to −10° C. and then pressurized with tetrafluoroethylene ($CF_2=CF_2$) which is first passed through a bubbler filled with α-pinene. The reaction is carried out at 60° C. under 60 psig to generate 97% (G.C. Area %) pure $CHF_2CF_2OCH_3$. No polytetrafluoroethylene is visually observed.

EXAMPLE 4

Preparation of Halogenated Ether Intermediates $$CF_3CHFCF_2OCH_3 + Cl_2 \xrightarrow{uv\ Light} CF_3CHFCF_2OCHCl_2 + CF_3CHFCF_2OCCl_3$$

This reaction is carried out in a jacketed glass photochemical reactor cooled with tap water. A medium pressure mercury lamp (100 watt, 11.49 watt total radiant energy) is used for the reaction. Chlorine gas is bubbled into 400 g of liquid $CF_3CHFCF_2OCH_3$ at 20° C.–30° C. and by-product HCl is vented to a water scrubber. The reaction is stopped, the crude reaction mixture is sampled, analyzed by gas chromatography, and then distilled. Two major products are generated in the reaction, $CF_3CHFCF_2OCHCl_2$ [37% (G.C. Area %), b.p. 75° C. @ 42 cmHg] and $CF_3CHFCF_2OCCl_3$ [61% (G.C. Area %), b.p. 82° C. @ 32 cmHg] for a total of 482 g of recovered crude material.

EXAMPLE 5

Preparation of Fluoroethers $$CF_3CHFCF_2OCHCl_2 + HF \xrightarrow{Cr/AC\text{—Gas phase}} CF_3CHFCF_2OCHF_2$$

50 g chromium/carbon catalyst is charged to a 0.5 inch×24 inch long Inconel® tubing reactor which is heated using radiant heat. After pre-fluorinating the catalyst, HF and 99.8% pure $CF_3CHFCF_2OCHCl_2$ are fed into a reactor at predetermined rates and temperature under atmospheric pressure. The crude product is collected in an ice water scrubber and washed with $H_2O$, dried over $MgSO_4$, and purified by distillation. The boiling point of the resulting $CF_3CHFCF_2OCHF_2$ is 47–48° C. and the density d=1.529. GC analysis of the collections corresponding to the parameters utilized are shown in the Table 3 below.

TABLE 3

Cr/AC - gas phase
$CF_3CHFCF_2OCHCl_2$ + HF → $CF_3CHFCF_2OCHF_2$

| | | HF/$R_f$OCHCl$_2$ | Contact time | G.C. Area % | | |
|---|---|---|---|---|---|---|
| Run | Temp. (° C.) | (mole ratio) | (sec) | $R_f$OCHF$_2$ | $R_f$OCHFCl | $R_f$OCHCl$_2$ |
| 1 | 120 | 7.6/1 | 17 | 95.6 | 1.11 | 0.23 |
| 2 | 125 | 6.2/1 | 21 | 99.2 | 0.05 | 0.003 |
| 3 | 150 | 7.8/1 | 12 | 98.3 | 0.23 | 0.003 |
| 4 | 150 | 6.0/1 | 11.6 | 98.8 | 0.05 | 0.927 |

$R_f = CF_3CHFCF_2$

EXAMPLE 6

Preparation of Fluoroethers $$CF_3CHFCF_2OCCl_3 + HF \xrightarrow{Cr_2O_3\text{—Gas Phase}} CF_3CHFCF_2OCF_3$$

38 g chromium (III) oxide catalyst† is charged to a 0.5 inch×14.125 inch long Inconel® tubing reactor which is heated by a ceramic fiber heater. The catalyst is dried under nitrogen at 250–300° C. After drying, the catalyst is prefluorinated at 250–300° C. using a HF:N$_2$ mixture (using a 1:20 dilution). This prefluorination is continued until HF is detected exiting the reactor. At this point, the nitrogen is turned off, and the temperature is increased to 350° C. The catalyst is held under these conditions for 16 hours. After pre-fluorinating the catalyst, HF and $CF_3CHFCF_2OCCl_3$ were fed into the reactor at predetermined rates and temperature under atmospheric pressure. The crude product is washed with $H_2O$, passed over calcium sulfate, and collected in a dry ice/acetone cooled trap. GC analysis of the reactor products corresponding to the parameters utilized are shown in the Table 4 below. The boiling point of the resulting $CF_3CHFCF_2OCF_3$ was 23–24° C.

TABLE 4

Cr$_2$O$_3$ - gas phase
$CF_3CHFCF_2OCCl_3$ + HF → $CF_3CHFCF_2OCF_3$

| Run | Temp. (° C.) | HF/$R_f$OCCl$_3$ (mole ratio) | Contact time (sec) | G.C. Area % | |
|---|---|---|---|---|---|
| | | | | $R_f$OCF$_3$ | $CF_3CHFCF_3$ |
| 1 | 150 | 6.04 | 8.66 | 4.28 | 15.78 |
| 2 | 175 | 7.12 | 8.13 | 62.00 | 12.21 |
| 3 | 200 | 7.12 | 8.09 | 71.89 | 13.67 |
| 4 | 200 | 10.87 | 19.27 | 72.58 | 15.41 |

TABLE 4-continued

| | | $Cr_2O_3$ - gas phase $CF_3CHFCF_2OCCl_3$ + HF → $CF_3CHFCF_2OCF_3$ | | | |
|---|---|---|---|---|---|
| | | | Contact | | |
| | | $HF/R_fOCCl_3$ | time | G.C. Area % | |
| Run | Temp. (° C.) | (mole ratio) | (sec) | $R_fOCF_3$ | $CF_3CHFCF_3$ |
| 5 | 200 | 21.07 | 8.43 | 77.06 | 12.01 |
| 6 | 250 | 8.0 | 6.58 | 30.4 | 52.23 |

$R_f$=$CF_3CHFCF_2$,
†Synetix ® CP200A catalyst, PO Box 1, Billingham, TS23 1 LB, UK

EXAMPLE 7

Preparation of Fluoroethers

Liquid Phase
$CF_3CHFCF_2OCCl_3$+HF $CF_3CHFCF_2OCFCl_2$ 405 g of $CF_3CHFCF_2OCCl_3$ produced according to the present invention is placed in a stainless steel pressure reactor. The reactor is cooled to −9° C. and 76 g of HF is added to the reactor. The reaction is carried out at 70° C., and a pressure of 300 psig is maintained in the reactor by venting the formed HCl to a water scrubber. 367.6 g crude product is collected. Gas chromatography analysis showed 91.1% (G.C. Area %) of $CF_3CHFCF_2OCFCl_2$, 3.6% (G.C. Area %) of $CF_3CHFCF_2OCF_2Cl$, and 3.5% (G.C. Area %) of unreacted $CF_3CHFCF_2OCCl_3$.

EXAMPLE 8

Preparation of Fluoroethers

Cr/AC—Gas Phase
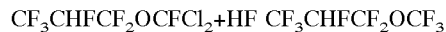
$CF_3CHFCF_2OCFCl_2$+HF $CF_3CHFCF_2OCF_3$

Similar set-up and procedure was used as in Example 6 above. After pre-fluorinating the catalyst, HF and 99% pure $CF_3CHFCF_2OCFCl_2$ are fed into a reactor at predetermined rates and temperature under atmospheric pressure. The resulting crude product is passed through a heated scrubber and collected in a trap cooled by dry ice/acetone. This liquid is then dried over $CaSO_4$ and GC analysis of the collected crude mixtures is shown in Table 5. The collected material is combined and distilled to give two fractions of $CF_3CHFCF_2OCF_3$ of 99.6% and 99.77% G.C. assay at a boiling point of 23–24° C.

TABLE 5

| | | Cr/AC - gas phase $CF_3CHFCF_2OCFCl_2$ + HF | | $CF_3CHFCF_2OCF_3$ | | |
|---|---|---|---|---|---|---|
| | | | Contact | | | |
| | | $HF/R_fOCFCl_2$ | Time | G.C. Area % | | |
| Run | Temp. (° C.) | (mole ratio) | (sec) | HFC-227ea | $R_fOCF_3$ | $R_fOCF_2Cl$ |
| 1 | 230 | 9.4/1 | 9 | 3.7 | 91.7 | 2.7 |
| 2 | 200 | 10/1 | 11 | 6.6 | 66.8 | 24.4 |

$R_f$=$CF_3CHFCF_2$

EXAMPLE 9

This example demonstrates the desirable "throw" obtainable with the fire suppression agents of the present invention when employed in portable ("streaming") applications. The throw is the distance the stream of agent can be discharged; the longer the throw the better, as this allows extinguishment without approaching the fire at too close a distance, which can lead to exposure of the operator to fire and toxic fumes from the combustion process.

A 150 mL SS cylinder is equipped with an inlet tube and a dip tube connected via an on/off valve to a delivery nozzle. The cylinder is charged with 50 grams of $CF_3CHFCF_2OCF_2H$ and then pressurized with nitrogen to the desired pressure. The cylinder contents are completely discharged and the throw distance noted (Table 6).

TABLE 6

Throw vs. Pressure for $CF_3CHFCF_2OCF_2H$ System

| Pressure, psig | Throw, feet |
|---|---|
| 25 | 10 |
| 80 | 15 |
| 120 | 17 |
| 150 | 18 |

EXAMPLE 10

This example demonstrates the extinguishment of Class B fires with the agents of the present invention. A 150 mL SS cylinder is equipped with an inlet tube and a dip tube connected via an on/off valve to a delivery nozzle. The cylinder is charged with 30 grams of $CF_3CHFCF_2OCF_2H$ and then pressurized with nitrogen to 120 psig. A 2 inch×4 inch×0.5 inch SS pan is filled with 20 mL of methanol. The methanol is ignited and allowed to burn for 30 seconds; the agent is then dischaged from a distance of 4 feet onto the fire. The methanol fire can be extinguished in 1.5 seconds; a total of 16 grams of agent was discharged.

EXAMPLE 11

The method of Example 10 is employed with acetone, isopropanol, and heptane fuels. All fires are rapidly extinguished (see Table 7).

TABLE 7

Extinguishment with $CF_3CHFCF_2OCF_2H$

| Fuel | Extinguishing Time, seconds | Agent discharged, Grams |
|---|---|---|
| Acetone | 2.0 | 25 |
| Isopropanol | 1.5 | 21 |
| Heptane | 1.8 | 11 |

EXAMPLE 12

This example demonstrates the extinguishment of deep-seated Class A fires with the agents of the present invention. A 150 mL SS cylinder is equipped with an inlet tube and a dip tube connected via an on/off valve to a delivery nozzle. The cylinder is charged with 30 grams of $CF_3CHFCF_2OCF_2H$ and then pressurized with nitrogen to 120 psig. A wood crib can be constructed of six layers of 6 inch×2 inch by 0.125 inch strips of kiln dried fir, each layer consisting of 4 pieces. The crib is soaked with heptane, ignited, and allowed to burn for five minutes. The agent is then discharged onto the fire, rapid (<2 seconds) extinguishment can be achieved; a total of 25 grams of agent is discharged. Immediately after extinguishment, the wood crib is cold to the touch, demonstrating the efficient suppression afforded by the agent.

EXAMPLE 13

$CF_3CHFCF_2OCF_3$ Cup Burner

Extinguishing concentrations of the hydrofluoroether $CF_3CHFCF_2OCF_3$ can be determined using a cup burner apparatus, as described in M. Robin and Thomas F. Rowland, "Development of a Standard Cup Burner Apparatus: NFPA and ISO Standard Methods, 1999 Halon Options Technical Working Conference, Apr. 27–29, 1999, Albuquerque, N.Mex." and incorporated herein by reference. The cup burner method is a standard method for determining extinguishing mixtures and has been adopted in both national and international fire suppression standards. For example, NFPA 2001 Standard on Clean Agent Fire Extinguishing Systems and ISO 14520-1: Gaseous Fire-Extinguishing Systems, both utilize the cup burner method.

A mixture of air and $CF_3CHFCF_2OCF_3$ is flowed through an 85 mm (ID) Pyrex chimney around a 28 mm (OD) fuel cup. A wire mesh screen and a 76 mm (3 inch) layer of 3 mm (OD) glass beads are employed in the diffuser unit to provide thorough mixing of air and $CF_3CHFCF_2OCF_3$.

n-Heptane is gravity fed to a cup from a liquid fuel reservoir consisting of a 250 mL separatory funnel mounted on a laboratory jack, which can allow for an adjustable and constant liquid fuel level in the cup. The fuel is ignited with a propane mini-torch and the chimney is placed on the apparatus. The fuel level is then adjusted such that fuel is 1–2 mm from the ground inner edge of the cup. A 90 second preburn period is allowed, and a primary flow of air is initiated via a calibrated flow meter @ 20–40 L/min.

Primary and secondary air flows are monitored by calibrated flow meters (210, 225, 230 and 240 tubes). The flows are maintained until the flames are extinguished. A constant primary flow (240 tube) between 20 to 40 L/min is maintained in all the tests. The secondary flow of air is passed through $CF_3CHFCF_2OCF_3$ contained in a 1150 ml steel mixing chamber equipped with a dip tube. The secondary flow, containing air saturated with $CF_3CHFCF_2OCF_3$, exits the mixing chamber and is mixed with the primary air flow before entering the cup burner's diffuser unit.

Immediately following flame extinction, a sample of the gas stream at a point near the lip of the cup is collected through a length of plastic tubing attached to a three way valve and multifit gas syringe. The sample is then subjected to gas chromatographic analysis (G.C.). G.C. calibration is performed by preparing standards samples in a 1L Tedlar® (E.I. DuPont De Nemours and Co. Corp., 1007 Market Street, Wilmington, Del.) bag.

A summary of test parameters and results are shown below in Table 8.

TABLE 8

Extinguishment of n-heptane Flames with $CF_3CHFCF_2OCF_3$

| Test | Primary Airflow (L/min) | $CF_3CHFCF_2OCF_3$ % (v/v) |
|---|---|---|
| 1 | 20.6 | 4.97 |
| 2 | 20.6 | 5.40 |
| 3 | 20.6 | 5.38 |
| 4 | 20.6 | 5.38 |
| 5 | 34.2 | 4.90 |
| 6 | 41.1 | 5.18 |
| 7 | 41.1 | 5.13 |
| 8 | 41.1 | 5.37 |
| 9 | 41.1 | 5.40 |
| 10 | 41.1 | 5.36 |

Additional objects, advantages, and other novel features of the invention will become apparent to those skilled in the art upon examination of the foregoing or may be learned with practice of the invention. The foregoing description of the embodiments of the invention has been presented for purposes of illustration and description. It is not intended to be exhaustive or to limit the invention to the precise form disclosed. Obvious modifications or variations are possible in the light of the above teachings. Embodiments were chosen and described to provide the best illustrations of the principals of the invention and their practical application, thereby enabling one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method for extinguishing a fire comprising the steps of introducing to the fire a fire extinguishing concentration of a composition comprising $CF_3CHFCF_2OCF_3$.

2. The method of claim 1, wherein the composition consists of $CF_3CHFCF_2OCF_3$.

3. The method of claim 1, wherein the composition is introducod at a level of at least about 3% (v/v).

4. The method of claim 1, wherein the composition is introduced from a total flooding system.

5. The method of claim 1, wherein the composition is introduced from a portable extinguishing system.

6. The method of claim 1, wherein the composition comprises a blend with other fire extinguishing agents.

7. The method of claim 6, wherein the other fire extinguishing agents are selected from the group consisting of $CF_3CHFCF_3$, $CF_3CF_2CF_2H$, $CF_3CH_2CF_3$, $CF_3CF_2H$, and $CF_3H$.

8. A method for one or more of extinguishing, suppressing or preventing a fire in a space by introducing to the space a mixture comprising $CF_3CHFCF_2OCF_3$.

9. The method of claim 8, wherein the mixture comprises about 0.1% (v/v) to about 10% (v/v) of the space.

10. The method of claim 8, wherein the $CF_3CHFCF_2OCF_3$ comprises from about 4% (v/v) to about 6% (v/v) of the space.

11. The method of claim 8, wherein the $CF_3CHFCF_2OCF_3$ comprises about 5% (v/v) of the space.

12. A fire extinguishing agent comprising, $CF_3CHFCF_2OCF_3$.

13. A composition comprising $CF_3CHFCF_2OCF_3$.

14. A mixture within a space comprising, $CF_3CHFCF_2OCF_3$.

15. The mixture of claim 14, wherein the mixture comprises about 0.1% (v/v) to about 10% (v/v) of the space.

16. The mixture of claim 14, wherein the $CF_3CHFCF_2OCF_3$ comprises from about 4% (v/v) to about 6% (v/v) of the space.

17. The mixture of claim 14, wherein the $CF_3CHFCF_2OCF_3$ comprises about 5% (v/v) of the space.

18. The mixture of claim 14, wherein the mixture consists essentially of $CF_3CHFCF_2OCF_3$.

19. The mixture of claim 14, wherein the mixture consists of $CF_3CHFCF_2OCF_3$.

20. A fire extinguishing, preventing or suppressing system configured to introduce to a space a mixture comprising $CF_3CHFCF_2OCF_3$.

21. The system of claim 20, wherein the mixture comprises about 0.1% (v/v) to about 10% (v/v) of the space.

22. The system of claim 20, wherein the $CF_3CHFCF_2OCF_3$ comprises about 4% (v/v) to about 6% (v/v) of the space.

23. The system of claim 20, wherein the $CF_3CHFCF_2OCF_3$ comprises about 5% (v/v) of the space.

* * * * *